United States Patent [19]

Niwa et al.

[11] Patent Number: 4,610,693
[45] Date of Patent: Sep. 9, 1986

[54] IMPLANTING ARTICLE MOLDED BY CENTRIFUGAL DISPERSION AND THE METHOD FOR PRODUCING THE SAME

[75] Inventors: Shigeo Niwa, Aichi; Junji Sugishita, Kuwana; Masami Ishii, Toyota, all of Japan

[73] Assignee: Aisin Seiki Kabushiki Kaisha, Kariya, Japan

[21] Appl. No.: 598,020

[22] Filed: Apr. 9, 1984

[30] Foreign Application Priority Data

Apr. 8, 1983 [JP] Japan .................................. 58-62795

[51] Int. Cl.⁴ .......................... A61F 2/02; A61F 2/28; A61F 2/32
[52] U.S. Cl. ......................................... 623/16; 164/97; 264/311; 128/92 C; 128/92 CA; 433/201.1; 501/1; 623/22; 623/23; 623/66
[58] Field of Search ........ 264/311; 128/92 C, 92 CA; 3/1.9, 1.912, 1.913; 501/1; 433/201; 164/97; 623/16, 22, 23, 66

[56] References Cited

U.S. PATENT DOCUMENTS

| 3,468,997 | 9/1969 | Pickels ................................... 164/97 |
| 4,051,598 | 10/1977 | Sneer .................................... 433/201 |
| 4,146,936 | 4/1979 | Aoyagi et al. ........................ 623/23 |
| 4,371,484 | 2/1983 | Inukai et al. ......................... 264/311 |
| 4,379,694 | 4/1983 | Riess .................................... 433/201 |
| 4,548,959 | 10/1985 | Nagai et al. ....................... 433/201.1 |

FOREIGN PATENT DOCUMENTS

| 1303139 | 4/1971 | Fed. Rep. of Germany . |
| 2546824 | 4/1977 | Fed. Rep. of Germany . |
| 2725665 | 12/1977 | Fed. Rep. of Germany . |
| 2905647 | 8/1980 | Fed. Rep. of Germany . |
| 2928007 | 1/1981 | Fed. Rep. of Germany ...... 433/201 |
| 54-138006 | 10/1979 | Japan ....................................... 3/1.9 |
| 57-118849 | 7/1982 | Japan .................................... 164/97 |
| 1380262 | 1/1975 | United Kingdom ................ 264/311 |

*Primary Examiner*—Helen M. McCarthy
*Attorney, Agent, or Firm*—Oblon, Fisher, Spivak, McClelland & Maier

[57] ABSTRACT

An implanting article which includes a base body composed of a mother material and a surface portion containing dispersed apatite particles. The base body and surface portion are formed in a mold by solidifying the mother material containing apatite particles under centrifugal force. The resulting implanting article has good mechanical properties because the base body scarcely includes apatite particles in addition the article has a good affinity with a live body because the surface portion contains apatite particles densely distributed thereat.

12 Claims, 23 Drawing Figures

FIG.1(a)  FIG.1(b)  FIG.1(c)
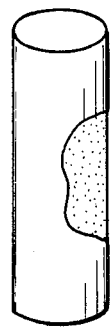  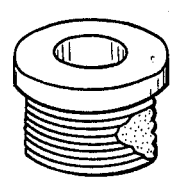
FIG.3
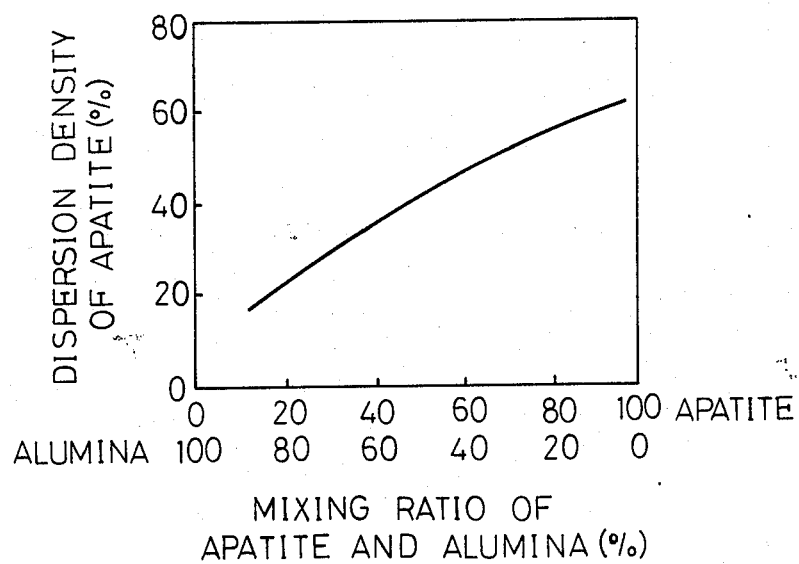

CHARPY IMPACT STRENGTH RATIO
TO DISPERSION WIDTH RATIO

CHARPY IMPACT STRENGTH RATIO
TO DISPERSION WIDTH RATIO ent's number: 4,610,693

IMPLANTING ARTICLE MOLDED BY CENTRIFUGAL DISPERSION AND THE METHOD FOR PRODUCING THE SAME

BACKGROUND OF THE INVENTION

1. Field of the Invention

The present invention relates to an improvement of an implanting article such as artifical bones, teeth root, etc.

2. Description of the Prior Art

As conventional implanting material using apatite, such prior arts is disclosed in Japanese published patent applications No. 50349/1980, "Dental compound material" and No. 45814/1981, "Hydroxy Apatite ceramic material and the manufacturing method thereof". Such state respectively that apatite has a favorable affinity with live bones, and also, a molded article made of a mixture of apatite and resin material can be used for an implanting article.

Apatite is a ceramic material mainly composed of calcium phosphate and, its mechanical strength and impact resistance are both poor. According to clinical experiences, apatite can be used only for covering broken parts of bone undergoing comparatively lower stress, but it is difficult for apatite to be applied to bone-joint portions or dental use.

Also, as described in the aforesaid "Dental compound material" (Japanese published patent application No. 50349/1980), articles prepared by homogeneously dispersing apatite particles in the mother material made from synthetic resin, etc. has been known.

The dental compound material may be molded into column shape artificial bones shown respectively in FIGS. 1(a), (b) and (c). The artificial bones are used as implanting articles for a thighbone. One of the dental compound materials is a mixture of polyethylene resin and apatite particles of 100 μm–500 μm in diameter. Another is an implanting material for dental use and is composed of a mixture of phenol resin and apatite particles.

However, these dental compound materials are a mixture of a mother material and apatite particles with a volmetric rate of from 9:1 to 4:6. The materials are molded into an artificial bone by heating while stirring, and finished to desired shapes. In this case, a required large density of apatite appeared on the surface of the resulting article is satisfied, but a great deal of apatite particles are also homogeneously dispersed to the center thereof (hereinafter this method is referred to as whole dispersion-manufacturing method).

Thus prepared artifical bones have poor strength, especially an inadequate impact resistance, so when these are used for long duration as an implanting article, deformation of breaking down may well occur. Accordingly, it was found that the processing for whole homogeneous dispersion of apatite over the mother material is not necesarily proper according to the kind of usage.

Moreover apatite dispersed into the center part of the artficial bones has no effect on affinity will organic bones, and also acts to lower the strength of the articles.

SUMMARY OF THE INVENTION

Therefore, the primary object of the present invention is to provide an implanting article which has good affinity with organic bones and high stability against stress.

Another object of the invention is to provide artificial inplanting articles having good affinity with organs and good mechanical properties.

A further object of the present invention is to provide a method for producing said artificial implanting articles.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 1(a), (b) and (c) illustrate, respectively a partially broken perspective view of a conventional implanting article wherein, FIG. 1(a) shwos a column shaped artificial bone, FIG. 1(b), one for dental use and FIG. 1(c), an artificial saucer-type hip dirarticulation prosthesis.

FIG. 3 is a graph which shows a relation between the apatite dispersion density and the mixing rate of apatite to alumina.

DESCRIPTION OF THE PREFERRED EMBODIMENTS

In the present invention, an unique centrifugal dispersion method is utilized to obtain a molded article, wherein a mixture of a mother material suited for implant use and apatite particles is put in a crucible or mold, and the crucible or mold is then rotated under centrifugal force of a gravity factor of 5G-3000G, and then heated, if necessary. As a result, due to the specific gravity (S.G.) difference between apatite and the mother material (about 3.1 for apatite, 0.9-1.4 for resins about 2.5 for aluminum series), apatite particles are dispersed in a surface layer portion, for example within a depth of 2 mm from the surface of the resulting article, and there is no dispersed apatite at the central portion of the article.

As the mother material, metals such as aluminum and aluminum alloys and synthetic resin may be employed. As the synthetic resin, phenol resin, polyester resin, urethane resin, epoxy resin, fluororesin, polysulfonic resin, polyethylene resin, polyamide resin, polypropylene resin, polyvinyl chloride resin, polycarbonate resin, polymethyl methacrylic resin, a mixture thereof and a copolymer composed of two or more of polymerizable monomers can be used.

As the dispersant, an apatite particle is used. Furthermore, by the experiments carried out by the inventors, it was found that blending inorganic powders such as alumina or aluminum powder with apatite increases the adherence strength between the dispersed apatite and mother material. Therefore a non-hazardous solid compound and metal can be used with apatite.

The size of the article to be produced is chosed depending on applicable parts. For artificial bones or joints, the preferable diameter of the article is 15-50 mm, and also, for artificial teeth, is approximately 4-10 mm.

For carrying out centrifugal molding, a mother material and dispersant are put into a mold or crucible together. The mother material for any form such as, for example block, particle or liquid may be used. As for the mother material of particle of liquid form, it is preferable to blend the mother material and dispersant homogeneously.

When a block is employed as the mother material, it is preferable that the block is shaped to match the central figure of an article to be produced, and the dispersant is put on the surface part where the dispersed apatite particles are to be contained.

The material in the mold or crucible, if necessary, is heated, that is, the heating is required in the case where the mother material is a solid one or a hardening reaction can proceed by heating. If the mother material is a solid, the mother material is heated over the melting point thereof.

Figure 10A:
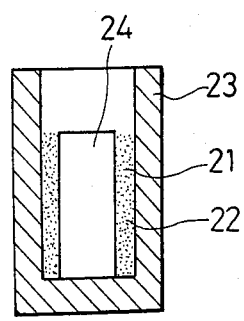
FIGS. 10(a) and (b) show a procedure outline of a centrifugal distribution method, in which aluminum alloy is used as the mother material.
Figure 10B:
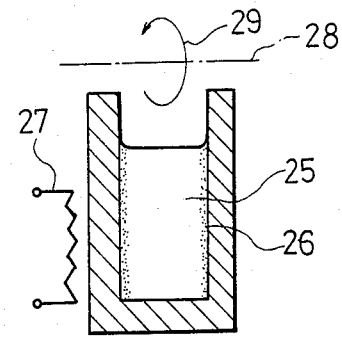

As for the rotation, there are three types:
(A) to rotate said mold or crucible with the central axis thereof being the rotational axis, as shown in FIG. 8(b),
(B) to rotate said mold or crucible with a rotational axis far from the mold or crucible as shown in FIG. 10(b),
(C) A combination of the aforementioned two ways.

Method (A) leads to the result that apatite particles are easily dispersed on the cavity bottom of said mold or crucible, so this method is suitable to produce an article having apatite concentrated at its bottom; the method according to (B) is suited to the case where apatite particles are dispersed mainly over the outer periphery of bar shaped articles.

When a block of mother material is placed in the center of the cavity of a mold, the dispersant is placed between the inner surface of the mold and the block, and rotation is carried out according to method (B). A bar shaped article having a peripheral surface layer portion rich in apatite particles dispersed therein may be obtained too.

The rotational velocity and time period of rotation are necessary factors for obtaining a desired dispersant settled surface layer portion. According to the article's strength and affinity with a live body, etc., it is not always preferable that a clear boundary be formed between the apatite dispersed surface layer portion and center portion mainly composed of the mother material.

A raw article can be obtained by solidifying the mother material during rotation of the mold. The resulting raw article is submitted to conventional machining such as cutting, etc. and finished as specified.

The thus prepared artificial implanting article has a structure composed of a surface layer portion where apatite or apatite and another dispresant exist in a dense distribution, and a central portion where the mother material or said mother material and the another dispersant are mainly included. The thickness of the surface layer portion is preferably of about 0.05-2 mm. As for the amount of apatite exposed over the surface layer, namely the density of the apatite is preferably 10%-90%. As the density of the apatite is elevated, the affinity thereof with a live body is increased, while the mechanical strength thereof is reduced. Furthermore, the boundary between the surface layer portion and central portion is preferably not clearly distinguishable. Namely it is preferable that dispersed apatite particles changes gradually towards the central portion.

The method of production will now be detailed as follows.

In the case where the mother material is a thermoplastic resin in a powdery state at a normal temperature, the resin powder and apatite particles are homogeneously mixed and put into a mold or crucible, and melted by heating. Thereafter, the mold or crucible is rotated around the central axis thereof under centrifugal force of a gravity factor of 50G-1000G, by cooling the mold or crucible and apatite particles are dispersed only over the thin surface layer of the resulting article.

In the case where the mother material is a thermosetting resin of a liquid state at a normal temperature (normal temperature setting resin being regarded as a type of thermosetting resin), the resin snd apatite are homogeously mixed and put into a mold or crucible, and the mold or crucible is rotated around the central axis thereof under centrifugal force of a Gravity Factor of 5G-100G. During the rotation, the thermosetting resin is cured. Thereby apatite particles are dispersed only over the thin surface layer of the resulting article. In order to cure the resin, some type of resin may be heated, and others mixed with a hardener (setting agent).

Figure 2:
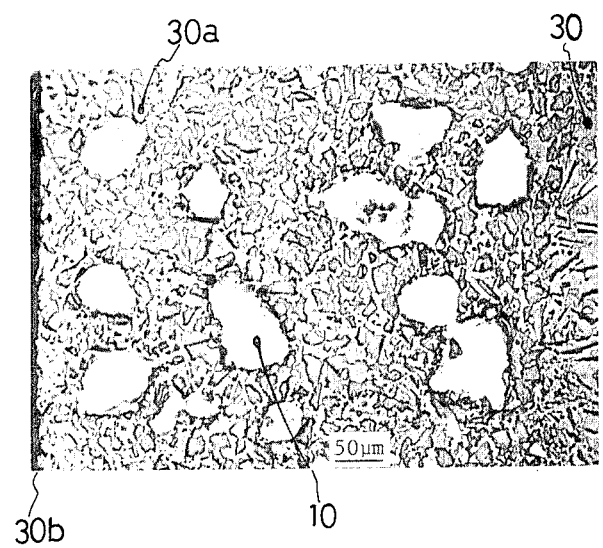
FIG. 2 is a microphotograph showing the micro structure of an article obtained in such way that apatite particle and alumina powder with a volumetric rate of 1:1 are mixed into aluminum alloy and is subjected to centrifugal dispersion.

When a metal such as aluminum, aluminum alloy, etc. is used as the mother material, a block or powder of the metal and the apatite particles are put into a mold or crucible. After being melted by heating the liquified metal is cooled in the mold or crucible. During cooling the mold or crucible is rotated such that the central axis of said mold or crucible is the rotation axis, and a centrifugal force is applied to the liquified metal and apatite particles, such that the apatite articles are dispersed only over the thin surface layer of the resulting article. The internal structure of the surface layer portion formed by the method is shown in the microphotograph of FIG. 2. Here, numerals 10, 30, 30a and 30b show respectively the apatite particle, the mother material, alumina particles and the surface of the article. The apatite particles and alumina particles are tightly surrounded by the mother material.

The apatite distribution density can be easily controlled by mixing another dispersant with apatite. FIG. 3 shows a relation between the apatite distribution density and the blending rate of apatite to alumina. Here, the compound material was composed of 60 volumetic percent aluminum and 40 volumetric percent of dispersant and the materials were heated up in a mold to 800° C., respectively. The centrifugal force was about 2000 G.

In the case where the resin is employed as the mother material, and mixture of aluminum powder with apatite particles is used as the dispersant, the mechanical properties such as hardness and compressive break down strength of the resulting article can be improved.

Figure 4:
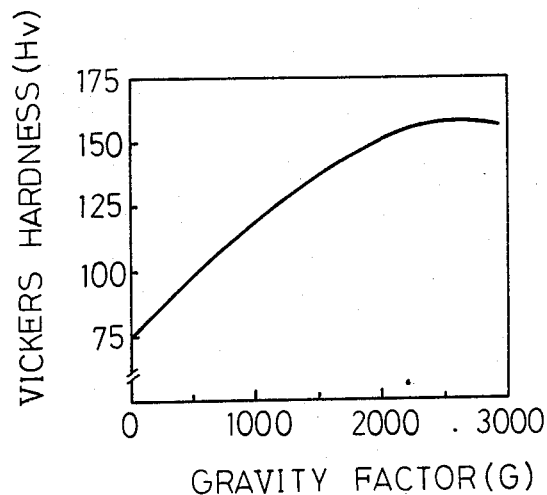
FIG. 4 is a graph which shows a relation between Vickers hardness of the surface layer dispersed with apatite and the Gravity Factor.

As for hardness, for the case where an aluminum alloy is utilized as the mother material, a relation between the Gravity Factor and Vickers hardness of the surface layer portion having apatite particles is shown in FIG. 4; Vickers hardness reaches the maximum value at a Gravity Factor of 2680G (at 800° C.), which is about two times that produced without gravity force.

Figure 5:
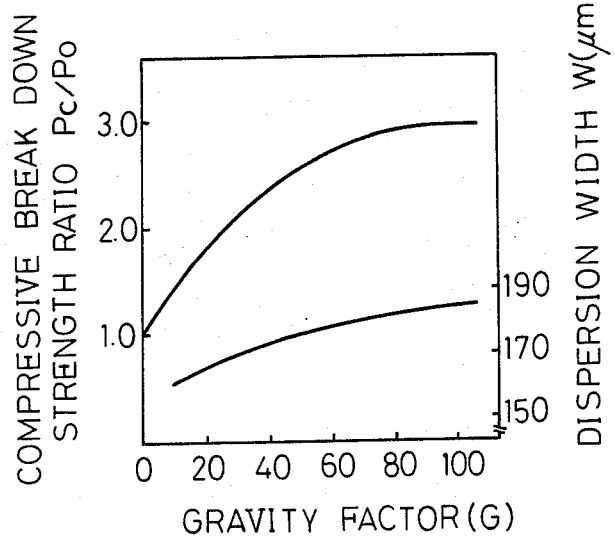
FIG. 5 is a graph which shows the relation between the dispersion width and the Gravity Factor and between the compressive break down strength ratio and the Gravity Factor.

In FIG. 5 is shown respectively the relation between the dispersion width W (A) and the Gravity Factor and the relation between the compressive break down strength ratio Pc/Po (B) and the Gravity Factor in the case where apatite is dispersed into polyester. According to FIG. 5, as the Gravity Factor increases, the compressive break down strength increases. For example, when the Gravity Factor is 80G, the compressive break down strength reaches about three times that produced under the Gravity Factor 0.

Figure 6:
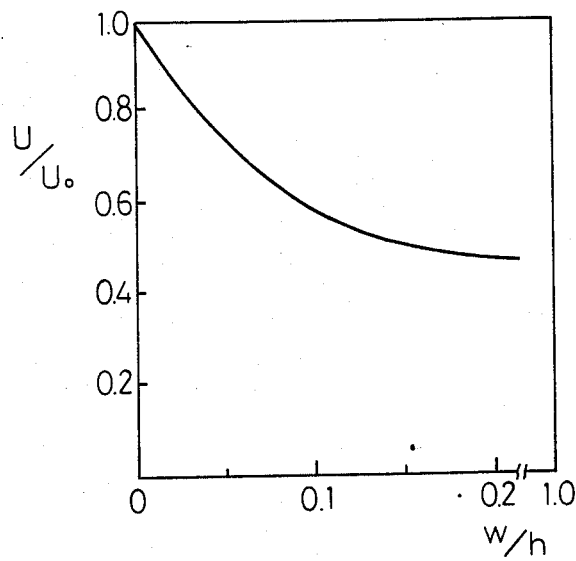
FIG. 6 is a graph which shows a relation between the Charpy impact strength ratio and the dispersion width ratio in the case where aluminum alloy is taken as the mother material.

As for the impact strength of the molded articles, the impart strength decreases according to the increase of the dispersion width of the article as shown in FIG. 6. In this case, aluminum alloy is employed as the mother material. In FIG. 6, the abcissa shows the dispersion width W ratio W/h to the diameter h of the molded article, while the ordinate shows the rate $U/U_0$ of the impact strength U of the molded article to the impact strength $U_0$ of the mother material itself.

Figure 7:
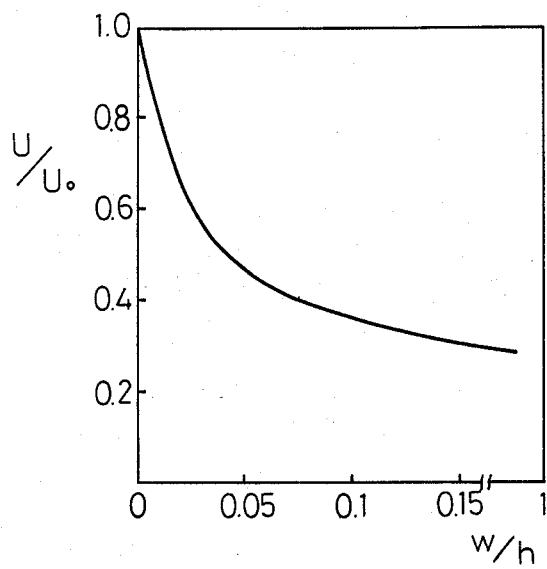
FIG. 7 is a graph which shows a relation between Charpy impact strength ratio and dispersion width ratio in the case where polyester is employed as the mother material.

According to FIG. 6, the impact strength at dispersion ration W/h=0.04 corresponds to about 80% of the impact strength of the mother material alone. The impact strength is about four times the impact strength of the article in which apatite is wholly dispersed (W/h—1.0). Similarly, the case where polyester is employed as the mother material is shown in FIG. 7. The impact strength of the article at which W/h is 0.02 is about 70 percent of that of the mother material alone. The impact strength is about four times of that of the article in which apatite is wholly dispersed.

Further, the centrifugal dispersion method of the present invention can produce an article having a multilayer structure of different mother materials along a radial direction of the rotation.

In the following discussion, embodiments of the present invention will be discribed.

EXAMPLE 1

Figure 8A:
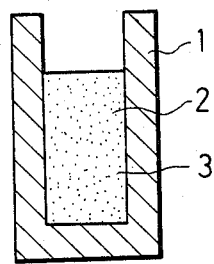
FIGS. 8(a) to (f) show a method for producing an implanting article to be implanted into a rabbit bone.
Figure 8B:
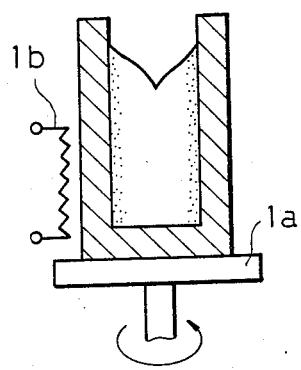
Figure 8C:
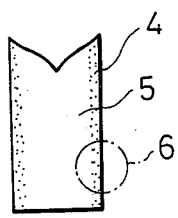
Figure 8D:
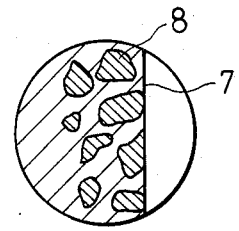
Figure 8E:
Figure 8F:
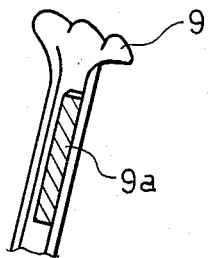

In FIG. 8(a)-(f) is shown a method in which apatite particle and a polyester resin monomer are used. Numeral 1 in FIG. 8(a) shows a stainless steel mold having about a 27 mm inner diameter and a 100 mm depth. 1.7 cubic centimeters of apatite particle of about 80 μm diameter and 50 cubic centimeters of liquid polyester resin monomer with hardening agent were blended and poured into the mold. Then the mold was fixed on a rotation stand and rotated at 1390 rpm around the mold center line. During the rotation mold was heated with the heater 1b to solidifying the polyester resin. This rotation produced a centrifugal force of 34G as a Graviry Factor at the peripheral surface portion of the resulting article. A cross sectional view of the raw article thus prepared is shown in FIG. 8(c). The article has a surface layer 4 dispersed with apatite and the center portion 5 absent from apatite. FIG. 8(d) shows an enlarged figure of portion 6 in FIG. 8(c). The numerals 7 and 8 in FIG. 8(d) show the surface of the article and dispersed apatite particle, respectively. The dispersion density of apatite at the surface layer 4 is about 60 percent; the dispersion width is about 100 μm and impact the strength is about 70 percent of that of the mother material. Next, a sample of 4 mm×2 mm×15 mm shown in FIG. 8(E) was cut off. The sample had the suface layer dispersed with apatite, the density of the apatite to the surface being about 50 percent. As shown in FIG. 8(f) the sample was implanted into a thighbone of a rabbit and taken out after one month of breeding.

Figure 9:
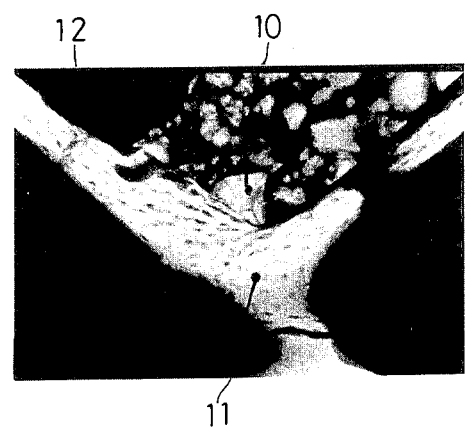
FIG. 9 is a photograph showing an enlarged physical structure of an implanting article and bone in which the article was implanted.

An enlarged physical structure photograph taken by means of microradiograph is shown in FIG. 9. The affinity of the sample with the bone 11 was good. Preferable bonding between the dispersed apatite and the bone was formed and there have been not found any rejection reaction against the foreign substance. Numeral 12 in FIG. 9 shows polyester resin used as the mother material.

EXAMPLE 2

In this embodiment, 30.5 grams of a bar-shaped aluminum alloy (AC3A) 24 was employed as the mother material and mixed with 0.75 cubic centimeters of apatite particle 21 was mixed with 0.75 cubic centimeters of alumina powder 22. Then the mixture was put into the space between the walls of the crucible having a 20 mm inner diameter and a 105 mm depth and the bar-shaped aluminum alloy 24 shown in FIG. 10(a). After the mixture was melted by heating at 700° C., the crucible was rotated as shown in FIG. 10(b). Numerals 28 and 29 show the rotation axis and the rotational direction, respectively. The rotational speed was 3500 rpm (about 2000G). During rotaion, the material was cooled to obtain a molded raw article.

In this case, the dispersion width of apatite and alumina was 1 mm; the dispersion density was 48 percent; Charpy impact strength was about 75 percent of the mother material alone. In FIG. 10(b), numerals 25 and 26 show a central portion and an apatite-aluminum dispersed surface layer portion respectively. A sample of 4 mm×2 mm×15 mm was cut off in a manner similar to that of example 1 and implanted into a rabbit's bone. When the physical structure was observed after one month, it has been affirmed that the sample was connected firmly with the rabbit's bone through the apatite in the surface portion of the sample and the adherence was high.

EXAMPLE 3

Figure 11A:
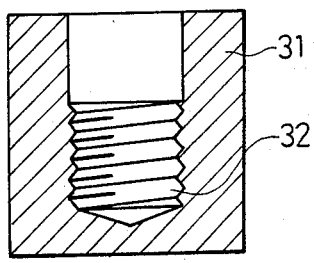
FIGS. 11(a), (b) and (c) respectively show a mold for artificial molar lid; the lid made therewith according to the centrifugal distribution method, and example of an application thereof.
Figure 11B:
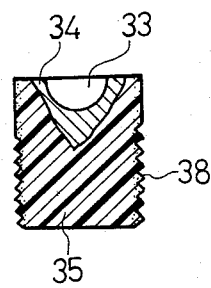

For an artificial molar lid available for an artificial crotch joint, a stainless steel mold 31 shown in FIG. 11(a) was employed. The mold was a split mold separable at a plane including the center line. The inner diameter of the mold 31 was 31 mm. The lower part thereof was provided with a screw 32 by means of cutting. In the mold was placed a liquid polyester monomer blended with 6 volume percent of apatite particle having about 80 μm diameter and 4 volume percent of gals fibers which were 6 mm long. Then the mold was rotated around the center line of the mold at 1366 rpm. The centrifugal force was about 40G at the inner surface of the mold. When the polyester monomer reached a semi-solid state, super high density polyethylene powder was put into the central space produced by rotation, melted by heating and solidified by cooling. Thus, a raw article for forming a molar lid socket part 33 was formed. The thickness of the surface layer portion of the resulting raw article was 0.23 mm. The density of apatite included in the surface layer portion was 50 percent. A molar lid shown in FIG. 11(b) was obtained by cutting the raw article. The molar lid comprises a solid portion with a dent 34 composed of super high density polyethylene, a central portion 35 composed of glass fiber reinforced polyester and a surface layer portion 38 having dispersed apatite particles.

Figure 11C:
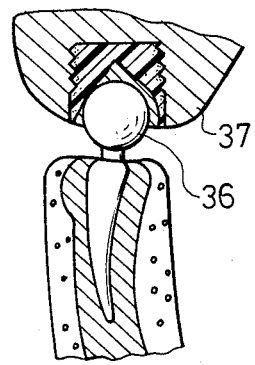

An application of the molar lid for a human body is shown in FIG. 11(c). The molar lid is implanted into a base bone for use an an artificial joint. The screw part formed on the surface layer portion with the dispersed apatite contact the base bone.

EXAMPLE 4

Figure 12A:
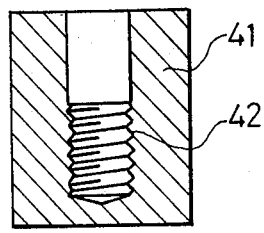
FIG. 12(a) shows a mold for artificial teeth roots.

A split mold 41 shown in FIG. 12 was used for producing an implanting article for dental use. The mold was made of stainless steel and has a screw 42 located at the lower part thereof. A bar shaped mother material was put in the center of the mold, a mixture of apatite particles and alumina particles in a volumetric ratio of 1:1 was put into the space between the wall and the mother material. After the material was melted by heating at about 700° C. the mold was rotated under about 3500 rpm (about 2000 G), utilizing the center line of the mold as its rotation axis. Thus, a dental implanting article having apatite dispersion width of 0.3 mm a dispersion density of 50 percent was obtained. The impact strength of the article was about 70 percent of that of the mother material alone. The article has satisfied the dental implanting requirement.

Figure 12B:
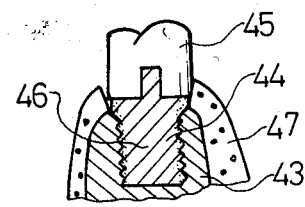
FIG. 12(b) shows an application example of the artificial teeth root made therewith according to the centrifugal distribution method.

In FIG. 12(b) is shown a practical application example. The example consist of an artificial tooth composed of a tooth root 46 and a tooth crown 46 fixed on the top of the tooth root 46. The tooth root 46 was made from the molded article. The artificial tooth was implanted into a chin bone 43 as shown in FIG. 12(b). Owing to the good affinity of the tooth root 46 with the chin bone 43, the artificial tooth was fixed firmly. In FIG. 12(b), numeral 47 shows a fresh tooth.

Obviously, numerous modifications and variations of the present invention are possible in light of the above teachings. It is therefore to be understood that within the scope of the appended claims, the invention may be practiced otherwise than as specifically described therein.

What is claimed is:

1. An implanting article to be implanted into a live body, comprising:
   a centrifugally cast base body including
   a surface portion which covers at least a portion of said base body
   wherein said base body includes a central portion composed mainly of a mother material suitable for implant use and
   wherein said surface portion comprises a surface layer portion containing dispersed apatite particles.

2. An implanting article according to claim 1, wherein said mother material comprises a metal.

3. An implanting article according to claim 2, wherein said metal is selected from the group consisting of aluminum and aluminum alloy.

4. An implanting article according to claim 1, wherein said mother material comprises a synthetic resin.

5. An implanting article according to claim 4, wherein said synthetic resin contains fibers for reinforcing said synthetic resin.

6. An implanting article according to claim 1, wherein the thickness of said surface portion is between 0.05 and 2 mm.

7. An implanting article according to claim 1, wherein the distribution density of the apatite included in said surface layer portion is from 10 to 90 volumetric percent.

8. An implanting article according to claim 1, wherein said surface layer portion includes a second dispersant.

9. An implanting article according to claim 8, wherein said second dispersant comprises alumina.

10. A method for producing an implanting article, which comprises;
    placing a mixture of mother material suitable for implant use and apatite particles having a different and greater specific gravity than that of said mother material into a mold,
    melting the mother material of said mixture;
    rotating said mold to apply a centrifugal force with a gravity force factor of 5G to 3000G to said mixture,
    solidifying said mixture under the application of said centrifugal force and
    removing a resulting solidified article out of said mold.

11. A method according to claim 10, wherein said step of rotating said mold comprises rotating said mold about a central axis thereof.

12. A method according to claim 10, wherein said mold is rotated about a rotational axis offset from said mold.

* * * * *